(12) United States Patent
Eaton et al.

(10) Patent No.: US 10,413,689 B2
(45) Date of Patent: Sep. 17, 2019

(54) ENDOSCOPIC AND TRANSESOPHAGEAL OROPHARYNGEAL AIRWAY

(76) Inventors: Peter David Eaton, Willow Street, PA (US); Lauren May Eaton, Oakland, CA (US)

( * ) Notice: Subject to any disclaimer, the term of this patent is extended or adjusted under 35 U.S.C. 154(b) by 313 days.

(21) Appl. No.: 13/543,739

(22) Filed: Jul. 6, 2012

(65) Prior Publication Data

US 2014/0007868 A1   Jan. 9, 2014

(51) Int. Cl.
| | |
|---|---|
| *A61M 16/00* | (2006.01) |
| *A61B 1/24* | (2006.01) |
| *A61M 16/04* | (2006.01) |
| *A61B 13/00* | (2006.01) |
| *A61F 5/56* | (2006.01) |

(52) U.S. Cl.
CPC .......... *A61M 16/0488* (2013.01); *A61B 1/24* (2013.01); *A61B 13/00* (2013.01); *A61F 5/566* (2013.01); *A61M 16/00* (2013.01); *A61M 16/0493* (2014.02); *A61M 16/0495* (2014.02)

(58) Field of Classification Search
CPC .. A61M 16/0488; A61M 16/04; A61M 16/16; A61M 16/00; A61M 16/0495; A61M 16/0493; A61M 2210/0643; A61M 16/049; A61M 16/0497; A61M 2202/064; A61B 1/24; A61B 13/00; A61B 17/32053; A61F 5/566; A47D 13/1115
USPC ............ 128/200.26, 204.18, 206.19, 204.14, 128/207.15, 207.16, 207.17, 859–862
See application file for complete search history.

(56) References Cited

U.S. PATENT DOCUMENTS

| | | | | |
|---|---|---|---|---|
| 3,568,680 | A | | 3/1971 | Raimo |
| 3,774,616 | A | * | 11/1973 | White ............... A61M 16/0488 128/200.26 |
| 3,856,001 | A | * | 12/1974 | Phillips ........................ 600/194 |
| 3,908,665 | A | * | 9/1975 | Moses ................... A61B 1/267 128/207.14 |
| 4,054,135 | A | * | 10/1977 | Berman ............ A61M 16/0488 128/200.26 |
| 4,067,331 | A | * | 1/1978 | Berman ............ A61M 16/0488 128/200.26 |
| 4,112,936 | A | * | 9/1978 | Blachly ............. A61M 16/0488 128/207.14 |
| 4,198,970 | A | * | 4/1980 | Luomanen ........ A61M 16/0488 128/207.15 |
| 4,270,531 | A | * | 6/1981 | Blachly ............. A61M 16/0488 128/207.14 |
| 4,453,905 | A | * | 6/1984 | Bennett ..................... 425/192 R |

(Continued)

*Primary Examiner* — Michael J Tsai
*Assistant Examiner* — Tu A Vo

(57) ABSTRACT

An oropharyngeal airway for use during diagnostic and surgical procedures, comprising a body with a proximal and a distal end. The distal end is sized for insertion through a protective bite block disposed in a patient's mouth. Both sides of the distal end are tapered to a curved distal edge. A flange is transversely opposed at the proximal end, preventing the proximal end from moving through the protective bite block and into the patient's mouth. An elliptically-arched channel in the shape of a lingual contour extends from the proximal end to the distal end. The channel includes a pair of tapered upstanding walls that guide the passage of a surgical instrument through the space between them. The oropharyngeal airway can be constructed of recyclable or biodegradable materials and is compatible with protective bite blocks of all sizes.

13 Claims, 8 Drawing Sheets

(56) References Cited

U.S. PATENT DOCUMENTS

| | | | | |
|---|---|---|---|---|
| 4,848,331 | A * | 7/1989 | Northway-Meyer | 128/200.26 |
| 5,024,218 | A | 6/1991 | Ovassapian et al. | |
| 5,355,874 | A * | 10/1994 | Bertram | A61M 16/0488 |
| | | | | 128/200.26 |
| 5,533,523 | A * | 7/1996 | Bass, Jr. | A61M 16/0488 |
| | | | | 128/859 |
| 5,590,643 | A * | 1/1997 | Flam | A61M 16/0488 |
| | | | | 128/200.26 |
| 6,196,224 | B1 * | 3/2001 | Alfery | A61M 16/0488 |
| | | | | 128/200.26 |
| 6,257,238 | B1 * | 7/2001 | Meah | 128/859 |
| 6,474,332 | B2 * | 11/2002 | Arndt | A61M 16/0488 |
| | | | | 128/200.26 |
| 6,517,549 | B1 * | 2/2003 | Dennis | 606/108 |
| 6,672,305 | B2 * | 1/2004 | Parker | 128/200.26 |
| 8,297,275 | B2 * | 10/2012 | Ogilvie et al. | 128/200.26 |
| 8,684,919 | B2 * | 4/2014 | Anca | A61M 16/0488 |
| | | | | 600/237 |
| 8,931,477 | B2 * | 1/2015 | Ogilvie | A61M 16/0488 |
| | | | | 128/200.26 |
| 2008/0000481 | A1 | 1/2008 | Ganesh et al. | |
| 2008/0156324 | A1 * | 7/2008 | Isenberg | A61M 16/0488 |
| | | | | 128/200.26 |
| 2009/0013995 | A1 | 1/2009 | Williams | |
| 2009/0050161 | A1 * | 2/2009 | Burdumy | 128/861 |
| 2009/0247892 | A1 * | 10/2009 | Castrodale | 600/543 |
| 2009/0318769 | A1 * | 12/2009 | Tenger et al. | 600/199 |
| 2010/0030027 | A1 * | 2/2010 | Bastid et al. | 600/120 |
| 2011/0126840 | A1 * | 6/2011 | Ogilvie | A61M 16/0488 |
| | | | | 128/207.14 |

\* cited by examiner

ENDOSCOPIC AND TRANSESOPHAGEAL OROPHARYNGEAL AIRWAY

FIELD

This disclosure relates to the establishment and maintenance of a patent airway during minimally invasive surgery, and, more particularly, to oropharyngeal airway devices used for such minimally invasive surgery.

BACKGROUND

The demand for the administration of anesthesia during minimally invasive surgery, in which a surgical instrument is disposed in the patient's upper airway, such as the esophagus or the airway structures distal to the glottic opening, and a protective bite block is placed into the mouth opening, has created airway maintenance issues that were not routinely encountered when these procedures were conducted with low level sedation or no sedation at all.

After induction of an anesthetic, particularly intravenous general anesthesia, upper airway tone is relaxed to such an extent that the upper airway may be blocked, preventing the anesthetized patient from spontaneously breathing. Specifically, the tongue typically relaxes in such a manner as to block the flow of air into and out of the lungs. Thus the airway is not patent.

In an effort to overcome this upper airway relaxation and to ensure that an anesthetized patient continues to spontaneously breathe, mechanical rescue maneuvers are often employed. If successful, a mechanical maneuver, such as a jaw thrust or a chin lift, which entails lifting the patient's chin and extending the neck, may encourage the relaxed tongue to move into a position anterior and superior to the glottic opening, thus allowing the free movement of air during spontaneous ventilation. The jaw thrust and other mechanical rescue maneuvers, however, are frequently unsuccessful in establishing and maintaining a patent airway. Depending on the depth of the anesthetic employed, the combination of pharmacologic agents administered, and the size of the patient's tongue, these mechanical rescue maneuvers may not ensure that the patient's airway will be established, remain patent, and that the patient will be able to spontaneously breathe.

During minimally invasive surgery, such as esophagogastroduodenoscopy, transesophageal echocardiography, or bronchoscopy, in which a surgical instrument, including fiberoptic scopes or ultrasound probes, is disposed in the patient's upper airway, a protective bite block is placed into the mouth opening. Such a bite block is placed between the upper and lower teeth acting as a barrier preventing injury to the patient's dentition and damage to the surgical instrument. Typically, a tubular access hole in the middle of the protective bite block allows for the passage of a surgical instrument into the oral cavity. The bite block is placed into the patient's mouth opening before the induction of an anesthetic; during this time, the patient is conscious and able to follow commands such as to open and close the mouth. The bite block does not incorporate a tongue blade to displace the tongue away from the glottic opening, so the gag reflex is not initiated. If the gag reflex were initiated, the disposition of a surgical instrument would be significantly impeded and the procedure uncomfortable for the patient to endure. However, after a protective bite block is in place and the induction of anesthesia has commenced, an anesthetized patient's gag reflex is obtunded, and the patient is thus typically able to comfortably tolerate the disposition of a surgical instrument into the upper airway, including but not limited to the esophagus or the airway structures distal to the glottic opening.

During minimally invasive surgery, the relaxed tongue of an anesthetized patient may obstruct the movement of air into and out of the glottic opening. When this occurs, the jaw thrust or chin lift rescue maneuvers may be employed to displace the relaxed tongue and to reestablish a patent airway, thereby allowing for spontaneous patient ventilation. In the event that these rescue maneuvers do not provide for the reestablishment and maintenance of a patent airway, the minimally invasive surgery must be abandoned, necessitating the complete removal of the surgical instrument from the oral cavity. Further, in order to reestablish the patent airway, an airway device must be inserted into the oropharyngeal cavity to displace the tongue away from the glottic opening.

Oral airway devices designed for insertion into the oropharyngeal cavity to displace the relaxed tongue away from the glottic opening often may not used with a protective bite block and surgical instrument in place. During minimally invasive surgery, including esophagogastroduodenoscopy, transesophageal echocardiography, or bronchoscopy, a protective bite block is placed into the mouth opening, and a surgical instrument, such as a fiberoptic scope or ultrasound probe, is disposed in the patient's upper airway. Oral airway devices may not be used in such minimally invasive surgery, because they will not physically fit into the mouth opening while a protective bite block and a surgical instrument are in place.

Further, the insertion of said oral airway devices through a protective bite block is difficult and often impossible due to size incompatibility with the bite block. To force the insertion of a larger than compatible airway device may cause physical harm to the patient's dentition and oropharyngeal airway structures. In practice, these incompatible oral airway devices may only be inserted, after removal of the surgical instrument and bite block, either with the aid of a tongue depressor or an upside-down insertion maneuver and 180-degree rotation into a position that displaces the relaxed tongue superior and anterior to the glottic opening. If the bite block were left in place in the patient's mouth opening, the use of a tongue depressor would likely cause injury to the side of the patient's mouth, because there is limited space between the side of the mouth and the bite block. Alternatively, the 180-degree rotation method, with the bite block in place, would also be hazardous, as damage to the roof of the patient's mouth would likely occur. Thus, there is a need for an oropharyngeal airway capable of safe insertion, while both a bite block and a surgical instrument are in place, without risking damage to a patient's mouth surface, dentition, or upper airway structures.

Further, existing oral airway devices are generally constructed of non-recyclable and non-biodegradable materials and are disposed of after a single use. The demand for the administration of anesthesia during minimally invasive surgery, and the frequency with which it is performed creates a need for a recyclable and biodegradable oropharyngeal airway.

For the safe and environmentally friendly administration of anesthesia during minimally invasive surgery, including but not limited to an esophagogastroduodenoscopy, transesophageal echocardiography, or bronchoscopy, such that the procedure would not have to be abandoned in order to reestablish a patent airway, there is a need for an oropharyngeal airway device compatible with a protective bite block and preferably composed of a recyclable or biodegradable material, that will allow for the maintenance of a patent airway and spontaneous ventilation.

SUMMARY OF PARTICULAR EMBODIMENTS

An oropharyngeal airway provides for the establishment and maintenance of a patent airway during the delivery of an anesthetic while a patient is undergoing minimally invasive surgery in which a surgical instrument is disposed in the upper airway, and a protective bite block is placed into the mouth opening.

In particular embodiments, an oropharyngeal airway may include a tapered body with distal and proximal ends. The distal end of the oropharyngeal airway may be inserted through a tubular access hole of a protective bite block. The body of the oropharyngeal airway may be an uninterrupted channel, which may be curved, from proximal end to distal end, to mimic a lingual curve. In particular embodiments, the body of the oropharyngeal airway may be a substantially U-shaped channel. In particular embodiments, the body of the oropharyngeal airway may be a radially-arched channel.

The oropharyngeal airway features a radially-arched channel, mimicking the lingual curve, such that it may be safely inserted straight forward, without the use of a tongue depressor or any need for rotation, techniques which create serious risk of injury to a patient's mouth surface, dentition, and upper airway structures. Further, the arched channel allows for disposition of the oropharyngeal airway so as to avoid pushing the tongue downward, obstructing the glottic opening, therefore establishing a patent airway once inserted.

The oropharyngeal airway of the present invention may also be composed of any suitable recyclable and/or biodegradable material, such as a starch-based biodegradable polymer.

DETAILED DESCRIPTION OF THE DRAWINGS

The scope of this disclosure is not limited to the example embodiments described or illustrated herein. The scope of this disclosure is also not limited to use in the contexts suggested by the background section.

Further, the terminology in this description is not intended to limit the disclosure. As used herein, the term "minimally invasive surgery" includes esophagogastroduodenoscopy, transesophageal echocardiography, bronchoscopy, or any other diagnostic or surgical procedure in which a surgical instrument is disposed in the oral cavity. Also as used herein, the term "surgical instrument" includes any one or more of flexible optical scopes, fiberoptic scopes, videoscopes, ultrasound probes, or other types of devices or combinations thereof, that are capable of performing functions ascribed to or associated with the surgical instrument.

Figure 1:
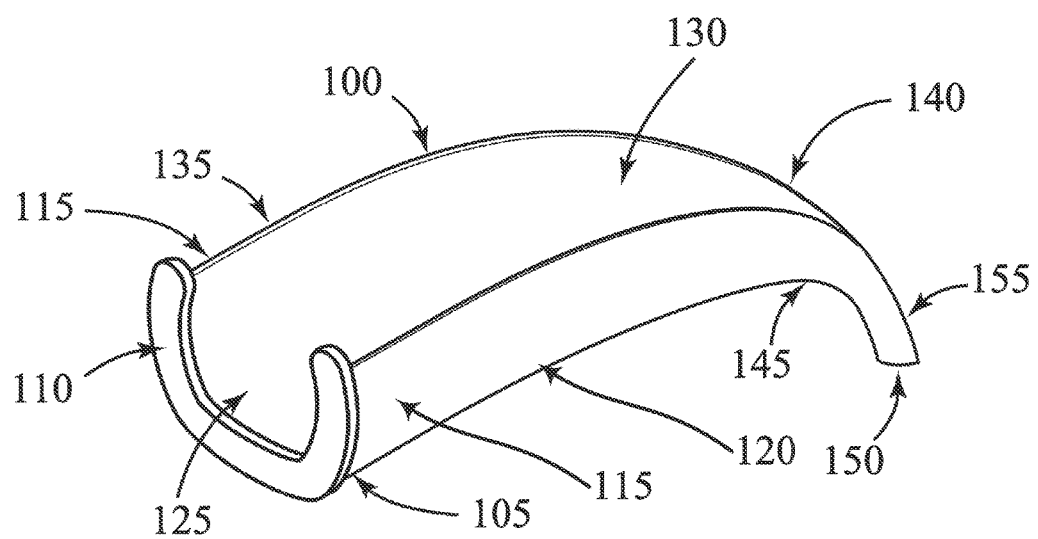
FIG. 1 is a perspective view of an oropharyngeal airway.
Figure 2:
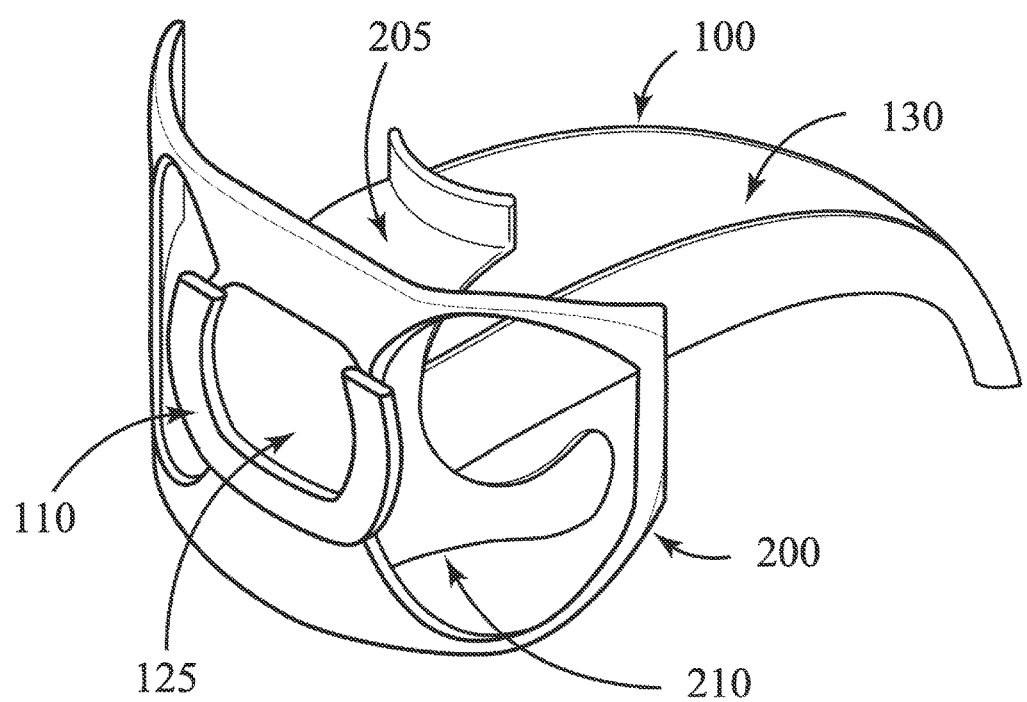
FIG. 2 is a perspective view showing an oropharyngeal airway disposed into a typical protective bite block.
Figure 3:
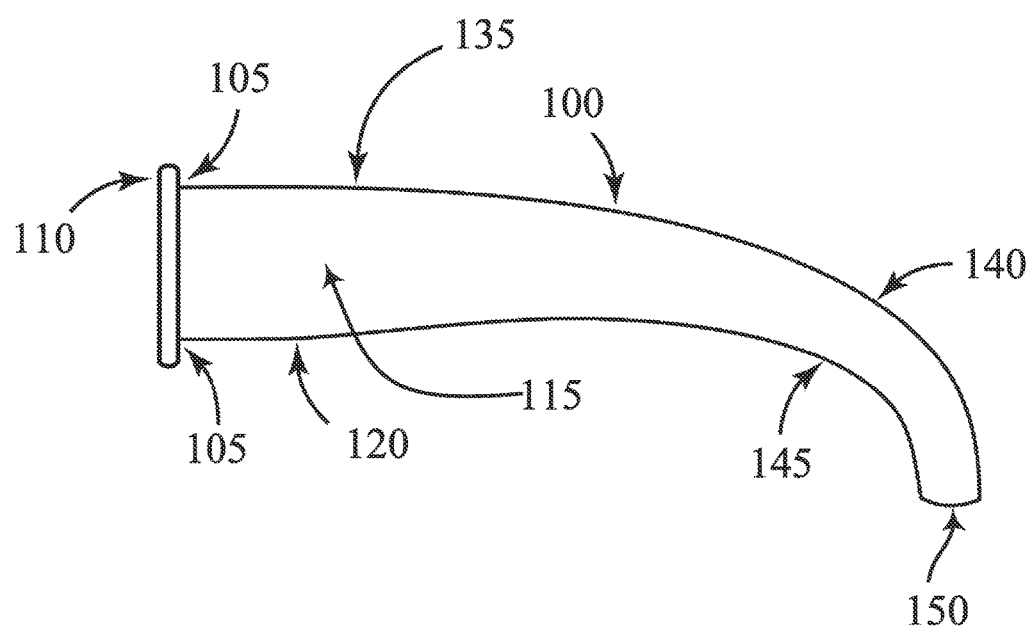
FIG. 3 is a side elevation view of an oropharyngeal airway.
Figure 4:
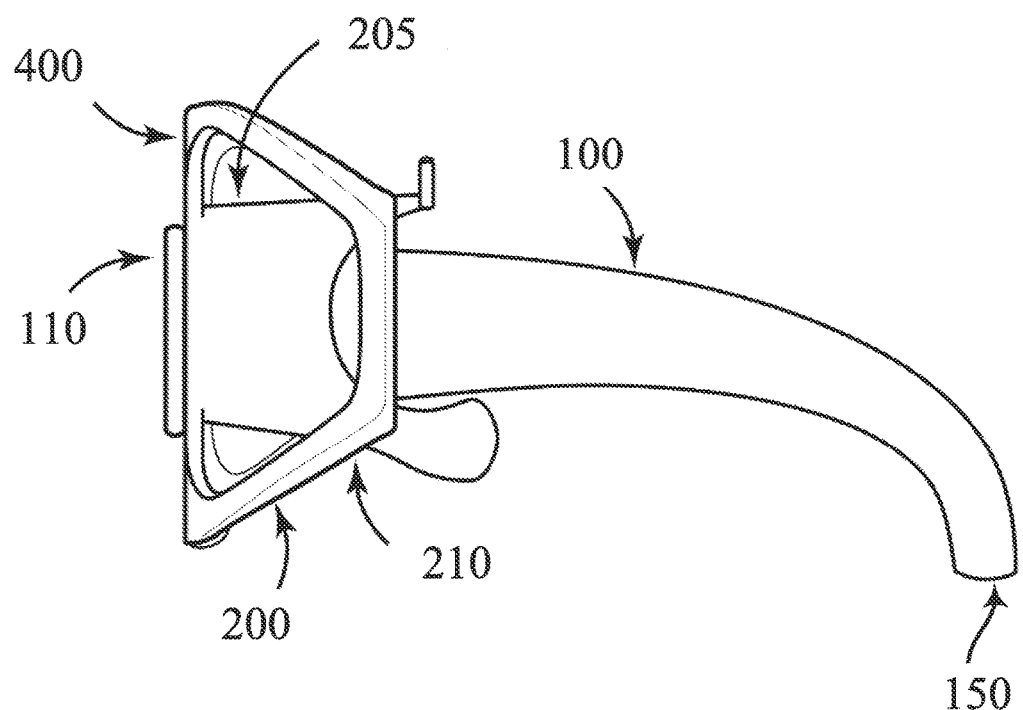
FIG. 4 is a side elevation view showing an oropharyngeal airway disposed into a typical protective bite block.

Referring now to the drawings in detail and particularly to FIGS. 1 and 3, there is shown one embodiment of an oropharyngeal airway 100 with an elongated, U-shaped channel 130, a transversely opposed flange 110 at the proximal end 105, and having a tapering distal end 150.

At the proximal end 105 and adjacent transversely opposed flange 110, there is a channel opening 125. In some embodiments, the airway 100 may be constructed of any suitable material, such as metal or plastic. In other embodiments, the airway may be constructed of any suitable recyclable or biodegradable material, such as a starch-based biodegradable polymer. Various embodiments of airway 100 can be in different sizes to accommodate protective bite blocks from different manufacturers and of differing sizes for use with patients of all ages and dimensions.

One embodiment of the airway 100, shown in FIGS. 1, 3, 7, and 8, has a radially-arched contour 145 that allows for the positioning of the tongue 820 in such a fashion as to establish and maintain a patent airway. The radially-arched contour mimics the lingual curve such that the airway may be safely inserted straight forward, without the use of a tongue depressor or any need for rotation, thus diminishing the risk of injury to a patient's mouth surface, dentition, and upper airway structures. Further, the embodiment's arched channel allows for disposition of the oropharyngeal airway so as to avoid pushing the tongue downward, obstructing the glottic opening, and therefore establishing a patent airway once inserted.

Figure 5:
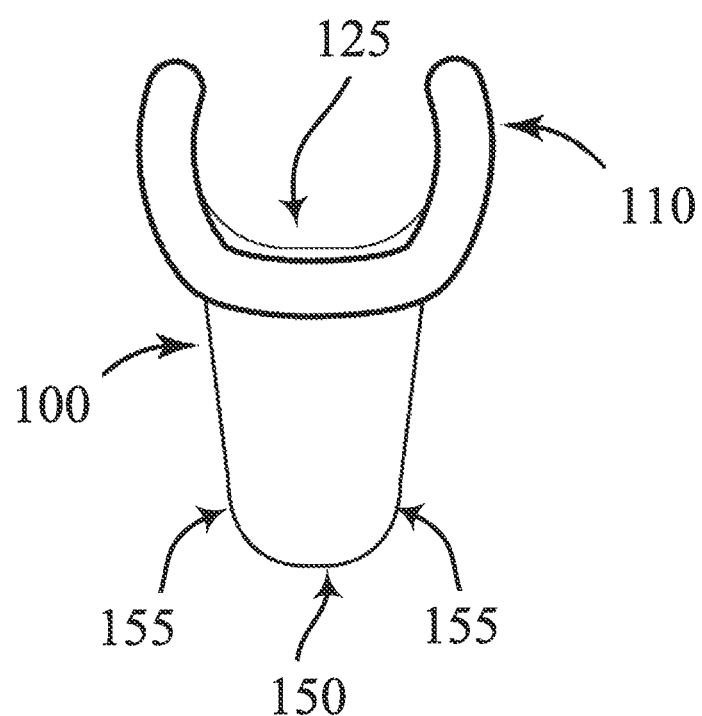
FIG. 5 is a front elevation view of an oropharyngeal airway.

Embodiments of the airway 100 include a tapered distal end 150 that allows for disposition of the distal end into the oropharyngeal cavity, while displacing the base of the tongue away from the glottic opening. The tapered distal end 150 allows for the tongue 820 to be moved anterior and superior to establish and maintain a patent glottic opening 830. An upstanding wall 115 extends from each side of the lingual surface 120 and is secured to the transversely opposed flange 110, as shown in FIGS. 1, 3, and 5. Upstanding wall 115 extends from each side from flange 110 to distal end 150, allowing and guiding the passage of a surgical instrument. In one embodiment, the height of upstanding walls 115 is consistent from points 105 to 135, and tapers along longitudinal, radial contour 140 from point 135 to distal end 150, shown in FIGS. 1 and 3.

Figure 6:
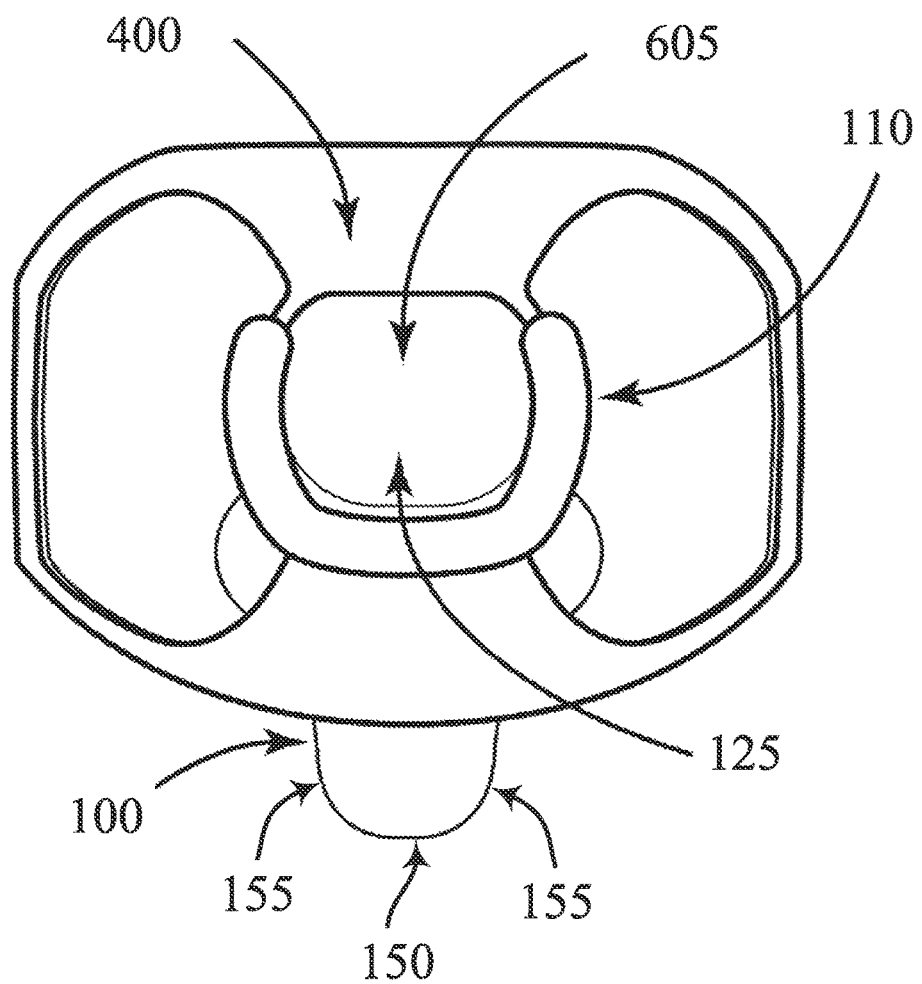
FIG. 6 is a front elevation view showing an oropharyngeal airway disposed into a typical protective bite block.
Figure 7:
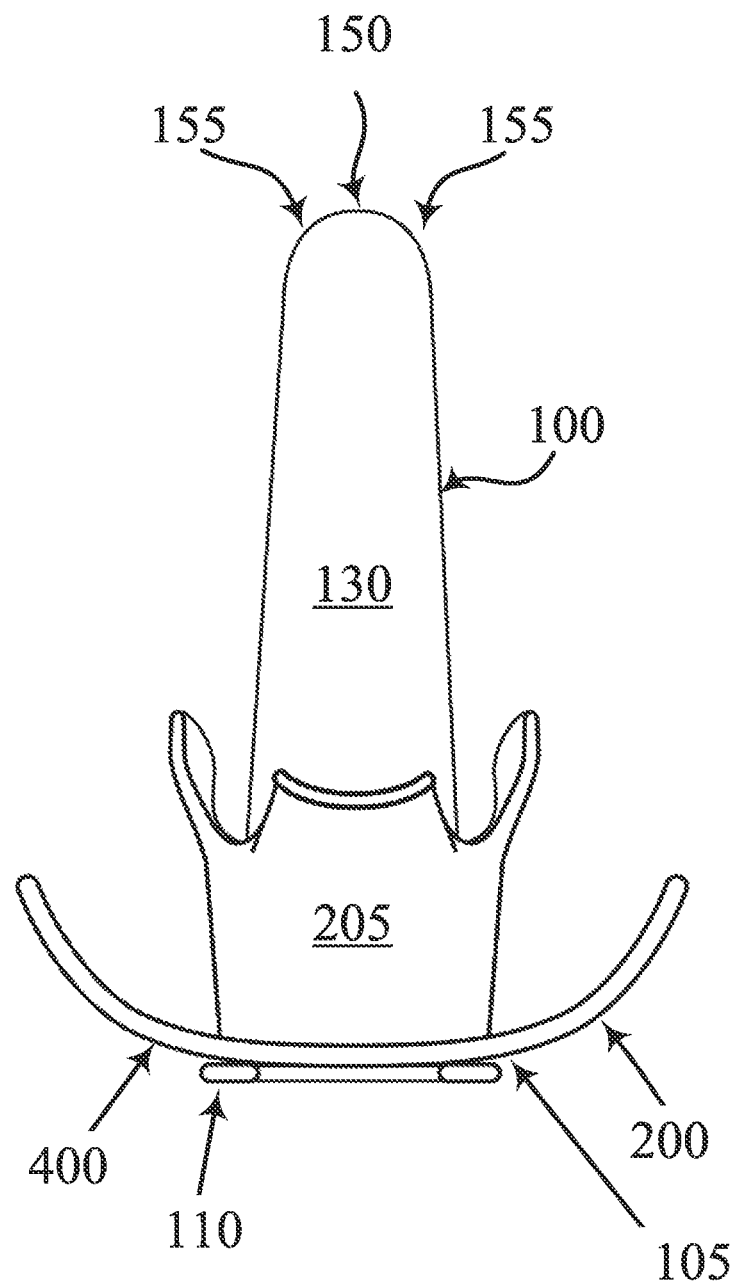
FIG. 7 is a top down view showing an oropharyngeal airway disposed into the typical protective bite block.
Figure 8:
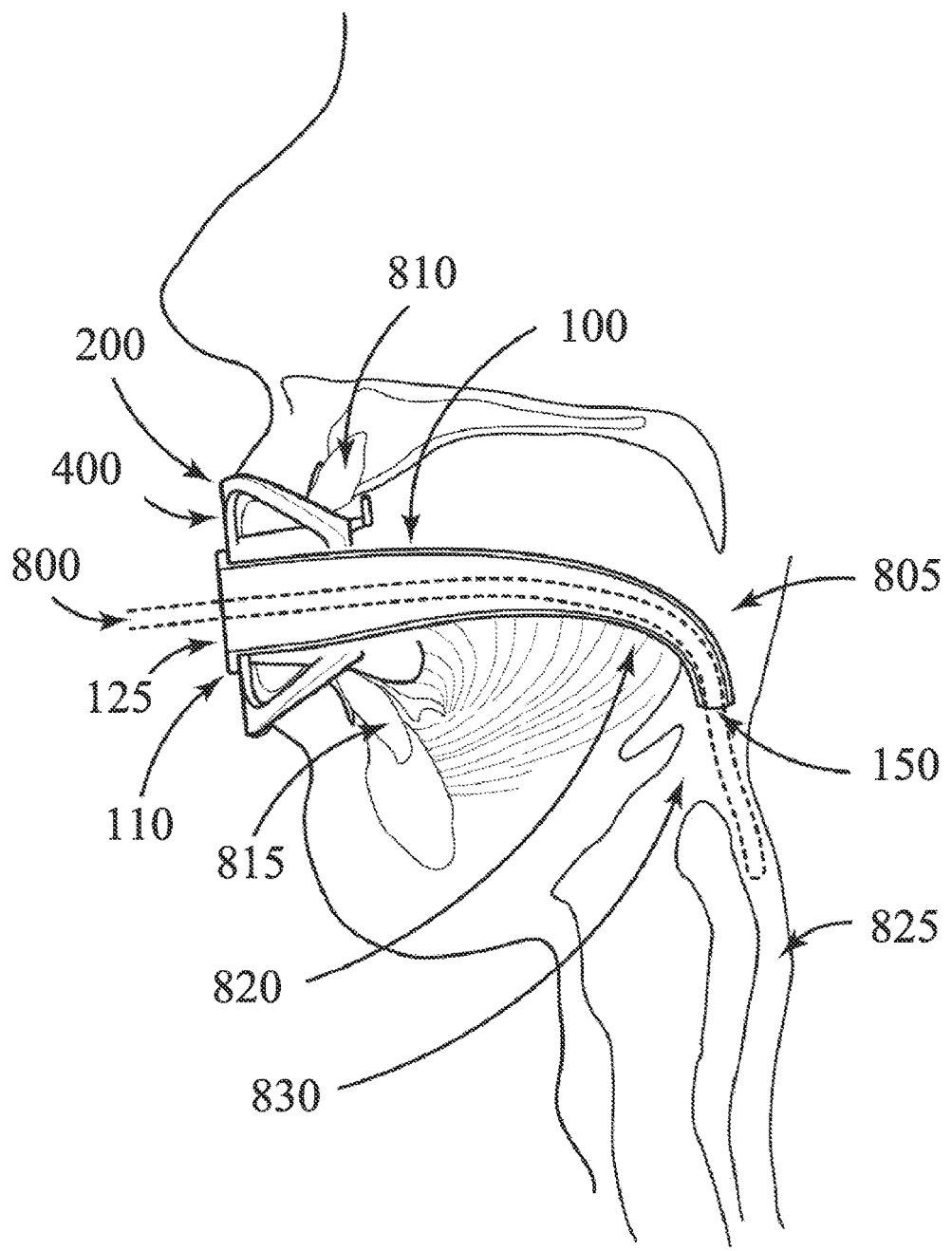
FIG. 8 is a profile view showing an oropharyngeal airway disposed in a typical protective bite block, placed in a patient's mouth opening with a surgical instrument concurrently disposed.

Referring now to FIGS. 5, 6, and 7, there is shown a radius taper 155 on both sides of the distal end 150 that forms a smooth distal edge and allows for the disposition of the airway 100 into the oropharyngeal cavity 805, shown in FIG. 8, without causing injury to contacted anatomical structures.

Referring now to FIGS. 2, 4, 6, 7, and 8, the airway 100 is shown disposed into a typical protective bite block 200. The oropharyngeal airway may be disposed into the oropharyngeal cavity while a protective bite block is in place at the mouth opening and either immediately preceding or any time after insertion of a surgical instrument.

Referring now to FIGS. 1, 2, 5, 6, and 8, channel opening 125, the U-shaped channel 130, radial contour 140, and radially-arched contour 145 allow the airway to be disposed into the oropharyngeal cavity during any said minimally invasive surgery with a protective bite block 200 disposed in the patient's mouth opening and a surgical instrument 800 in place.

Referring now to FIGS. 2, 4, 6, and 8, there is shown a structure consistent with a typical protective bite block 200. The patient's upper teeth or gums 810 rest on surface 205, while the patients lower teeth or gums 815 rest on surface 210. The surgical instrument 800 is introduced and disposed through the tubular access hole 605 into the oropharyngeal cavity 805 and the esophagus 825. The distal surface of flange 110 rests on the outer plane 400, preventing disposition of the entire airway 100 into the oral cavity. In one embodiment, the oropharyngeal airway includes a U-shaped flange, at the proximal end, which prohibits the proximal end from moving through the bite block and into the oral cavity Referring now to FIG. 8, the human profile shown demonstrates the disposition of the airway 100 in the oropharyngeal cavity 805 with protective bite block 200 disposed at the mouth opening and a surgical instrument 800 disposed in the esophagus 825.

Numerous characteristics, advantages, and embodiments of the invention have been described in detail in the foregoing description with reference to the accompanying drawings. However, the above description and drawings are illustrative only. The present invention is not limited to the illustrated embodiments, and all embodiments of the invention need not necessarily achieve all of the advantages or purposes, or possess all characteristics, identified herein. One skilled in the art may effect various changes and modifications without departing from the scope or spirit of the present invention. Although example materials have been provided, the invention is not limited to such materials unless specifically required by the language of a claim. The elements and uses of the above-described embodiments can be rearranged and combined in manners other than specifically described above, with any and all permutations within the scope of the invention. The present invention should not be limited to any single embodiment, but rather should be constructed in breadth and scope in accordance with the recitation of the appended claims.

We claim:

1. A device comprising: a protective bite block; an oropharyngeal airway, wherein the oropharyngeal airway comprising: a distal end and a proximal end, wherein:
   the distal end of the oropharyngeal airway is adapted for removable insertion through an access hole of the protective bite block,
   the distal end of the oropharyngeal airway is adapted for disposal into an oropharyngeal cavity of a patient, and
   the proximal end of the oropharyngeal airway is adapted for disposal at the access hole;
   a radially-arched channel comprising a lingual surface and a pair of upstanding walls extending longitudinally along the lingual surface, wherein:
      the radially-arched channel has a curve, the curve being adapted to a lingual contour, wherein the curve is directed to the oropharyngeal cavity,
      the radially-arched channel extends between the proximal end of the oropharyngeal airway and the distal end of the oropharyngeal airway,
      the radially-arched channel has a length, the length being made up of a first portion of the length and a second portion of the length, the second portion of the length being greater than the first portion of the length,
      a height of the pair of upstanding walls tapers longitudinally down the second portion of the length of the radially-arched channel,
      the radially-arched channel does not comprise an injection channel positioned at any on the radially-arched channel extending between the proximal end of the oropharyngeal airway and the distal end of the oropharyngeal airway, and the radially-arched channel has a substantially U-shaped cross-section; and a flange, wherein the flange is disposed at the proximal end of the oropharyngeal airway, and wherein the flange abuts the protective bite block, the proximal end of the oropharyngeal airway being prevented from moving through the access hole and from entering the oropharyngeal cavity of the patient by the flange, and wherein the flange extends uninterrupted along a U-shaped edge of the pair of upstanding walls and the lingual surface at the proximal end of the oropharyngeal airway.

2. The device of claim 1, wherein the tapering of the height of the pair of upstanding walls longitudinally down the second portion of the length of the radially-arched channel is adapted for removable disposal of the oropharyngeal airway into the oropharyngeal cavity of the patient and for prevention of injury to the oropharyngeal cavity of the patient during the removable disposal.

3. The device of claim 1, wherein the distal end of the oropharyngeal airway is radially tapered, the distal end of the oropharyngeal airway comprising a smooth distal edge.

4. The device of claim 1, wherein the height of the pair of upstanding walls tapers longitudinally down a radial contour, the radial contour being adapted to the lingual contour, and wherein the radial contour extends along the second portion of the length of the radially-arched channel.

5. The device of claim 1, wherein the oropharyngeal airway is comprised of a recyclable material.

6. The device of claim 1, wherein the oropharyngeal airway is comprised of a biodegradable material.

7. The device of claim 1, wherein the oropharyngeal airway is comprised of a starch-based biodegradable polymer.

8. The device of claim 1, wherein the orophatyngeal airway is adapted for straight-forward insertion of the distal end of the oropharyngeal airway through the protective bite block and into the oropharyngeal cavity of the patient, the oropharyngeal airway being adapted to prevent injury to the oropharyngeal cavity of the patient during the straight-forward insertion.

9. The device of claim 1, wherein the oropharyngeal airway is adapted for insertion of the distal end of the oropharyngeal airway through the protective bite block, into the oropharyngeal cavity of the patient after a surgical instrument has been disposed through the bite block and into the oropharyngeal cavity of the patient, the oropharyngeal airway being adapted to prevent injury to the oropharyngeal cavity of the patient during the insertion and to prevent damage to the surgical instrument by the insertion.

10. The device of claim 1, wherein the curve of the radially-arched channel is gradual at the proximal end of the oropharyngeal airway and steep at the distal end of the oropharyngeal airway, the curve being adapted for straight-forward insertion of the distal end of the orophatyngeal airway through the protective bite block and into the oropharyngeal cavity of the patient, the curve being adapted to prevent injury to the oropharyngeal cavity of the patient during the straight-forward insertion.

11. The device of claim 1, wherein the proximal end of the oropharyngeal airway has a U-shaped cross-section.

12. The device of claim 1, wherein the second portion of the length of the radially-arched channel comprises the distal end of the oropharyngeal airway, and wherein the first portion of the length of the radially-arched channel comprises the proximal end of the oropharyngeal airway.

13. The device of claim 12, wherein the curve of the radially-arched channel has a first curved portion along the first portion of the length of the radially arched channel and a second curved portion along the second portion of the length of the radially-arched channel, and wherein a magnitude of a slope of the second curved portion is greater than a magnitude of a slope of the first curved portion.

* * * * *